United States Patent [19]

Young

[11] 4,040,421
[45] Aug. 9, 1977

[54] HYPODERMIC SYRINGE AND ATTACHED NEEDLE ASSEMBLY

[75] Inventor: H. Theodore Young, Union, N.J.

[73] Assignee: Becton, Dickinson and Company, Rutherford, N.J.

[21] Appl. No.: 702,914

[22] Filed: July 6, 1976

Related U.S. Application Data

[63] Continuation-in-part of Ser. No. 565,048, April 4, 1975, abandoned.

[51] Int. Cl.² ............................................. A61M 5/00
[52] U.S. Cl. ............................. 128/218 N; 128/221
[58] Field of Search ....... 128/218 N, 218 NV, 218 R, 128/214.4, 220, 221, 215, 247

[56] References Cited

U.S. PATENT DOCUMENTS

| | | | |
|---|---|---|---|
| 2,755,801 | 7/1956 | Morando | 128/218 N |
| 3,756,235 | 9/1973 | Burke et al. | 128/218 N |
| 3,851,647 | 12/1974 | Monestere, Jr. et al. | 128/214.4 |

FOREIGN PATENT DOCUMENTS

| | | | |
|---|---|---|---|
| 661,018 | 3/1965 | Belgium | 128/218 R |
| 1,224,269 | 6/1960 | France | 128/218 N |
| 998,648 | 1/1952 | France | 128/218 N |
| 867,972 | 5/1961 | United Kingdom | 128/218 NV |
| 4,104 | 4/1899 | United Kingdom | 128/218 N |

Primary Examiner—John D. Yasko
Attorney, Agent, or Firm—Kane, Dalsimer, Kane, Sullivan and Kurucz

[57] ABSTRACT

The connection joint attaching the needle assembly to the hypodermic syringe includes a female conical opening in the reduced boss of the barrel and a male conical extension of the hub which corresponds in dimensions such that when the conical extension is inserted into the conical opening, the proximal end of the extension will be substantially flush with the inner end wall of the barrel. At the same time, a substantially leakproof seal between such conical surfaces is provided whereby there will be no residual volume of liquid beyond the measured amount in the barrel when a piston is extended fully into the barrel against the end wall and there will be no leakage of the liquid between the juncture of such conical surfaces. A tubular collar is provided with an inwardly extending radial ring or bead which firmly and frictionally engages with the outer surfaces of the reduced boss on the syringe barrel to provide a mechanical lock of the needle assembly. In time, the radial bead forms a corresponding depression or detent in the outer surface of the reduced boss thereby preventing the needle assembly from disassociating with the syringe barrel either during removal of the needle sheath or during the liquid injection process.

1 Claim, 6 Drawing Figures

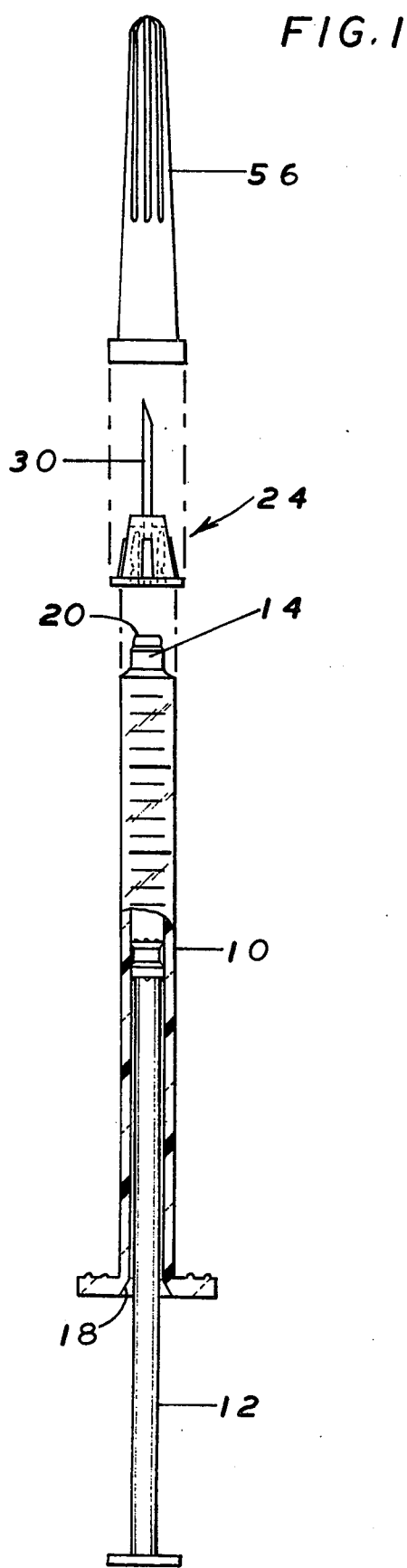
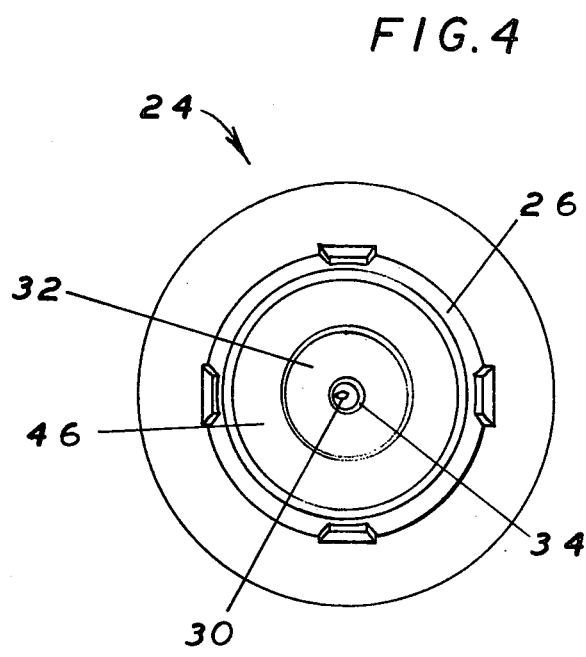
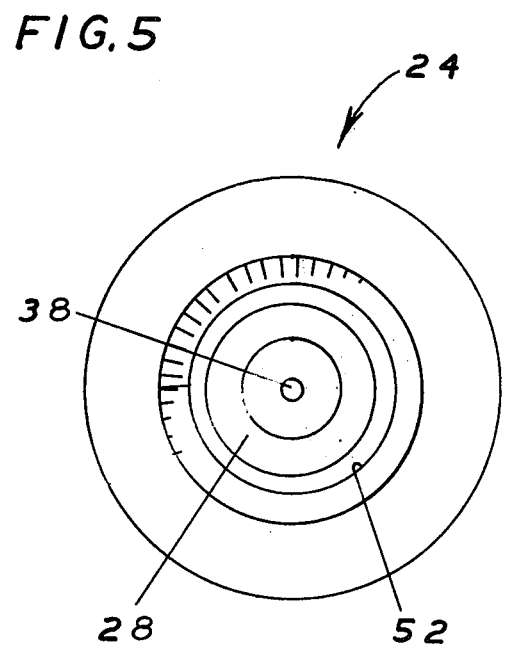

HYPODERMIC SYRINGE AND ATTACHED NEEDLE ASSEMBLY

CROSS-REFERENCE TO RELATED APPLICATION

This application is a continuation-in-part of commonly assigned application Ser. No. 565,048 filed Apr. 4, 1975 now abandoned.

BACKGROUND OF THE INVENTION

The present invention relates to improvements in low-dose hypodermic syringes and more particularly to the joint connection to attach the needle assembly to the barrel of the syringe.

In low-dose syringes, parts are normally small while generated forces during injection are comparatively high. Problems have been experienced in initially creating a liquid tight seal between the parts of the needle assembly and syringe barrel and maintaining it during removal of the needle sheath and while injecting the contained liquid. When dealing with syringes of ½ cc and less capacity, accuracy in amount of liquid injected becomes critical in assuring proper medication and therapy.

The standard luer connection in frequent use today is not entirely satisfactory for low-dose syringes and also has an internal volume significantly beyond the main barrel chamber so that the syringe must be filled with excess medicament to compensate for this volume when measuring dosage. After administration, this residual volume of medicament remains in the syringe tip and needle hub lumen. When two or more medicaments are measured in the same syringe, the excess or residual volume will create an error of their relative ratio in the resultant mixture.

SUMMARY OF THE INVENTION

It is an object of the present invention to provide a low-dose hypodermic syringe and attached needle assembly with an improved connection joint which securely attaches the needle assembly to the barrel of the syringe.

It is a further object to provide such a connection of the needle assembly to the barrel of a syringe wherein the needle assembly will not disassociate from the syringe barrel while removing the needle sheath nor during the injection process and wherein the proximal end of the needle hub is flush with the roof of the fluid chamber of the barrel to eliminate any substantial residual volume of fluid over the measured volume of the syringe.

It is a further object to provide such a connection of the type described which operates in an efficient manner and is simple to manufacture and use.

BRIEF DESCRIPTION OF THE DRAWINGS

Other objects and advantages will become apparent from the following detailed description of a somewhat preferred embodiment of the invention which is to be taken in conjunction with the accompanying drawings in which:

FIG. 1 is an exploded view illustrating the parts of the hypodermic syringe and needle assembly;

FIG. 4 is a front end view of the needle assembly;

FIG. 5 is a rear end view of the needle assembly; and

DESCRIPTION OF THE PREFERRED EMBODIMENT

Figure 2:
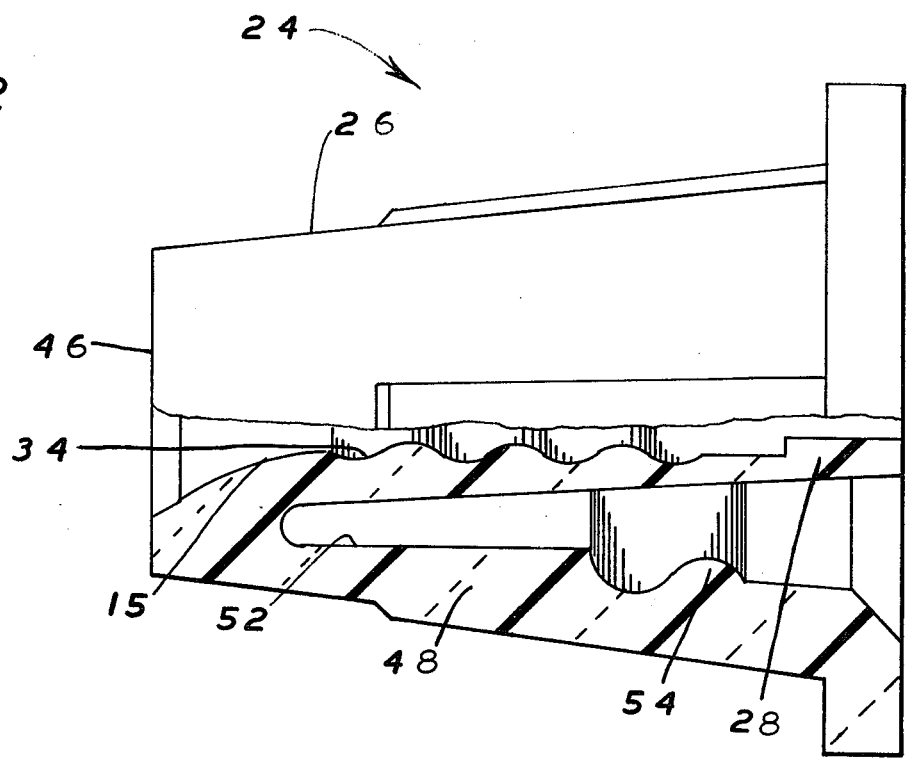
FIG. 2 is an enlarged elevational view of the needle hub partly broken away and sectioned for clarity.
Figure 3:
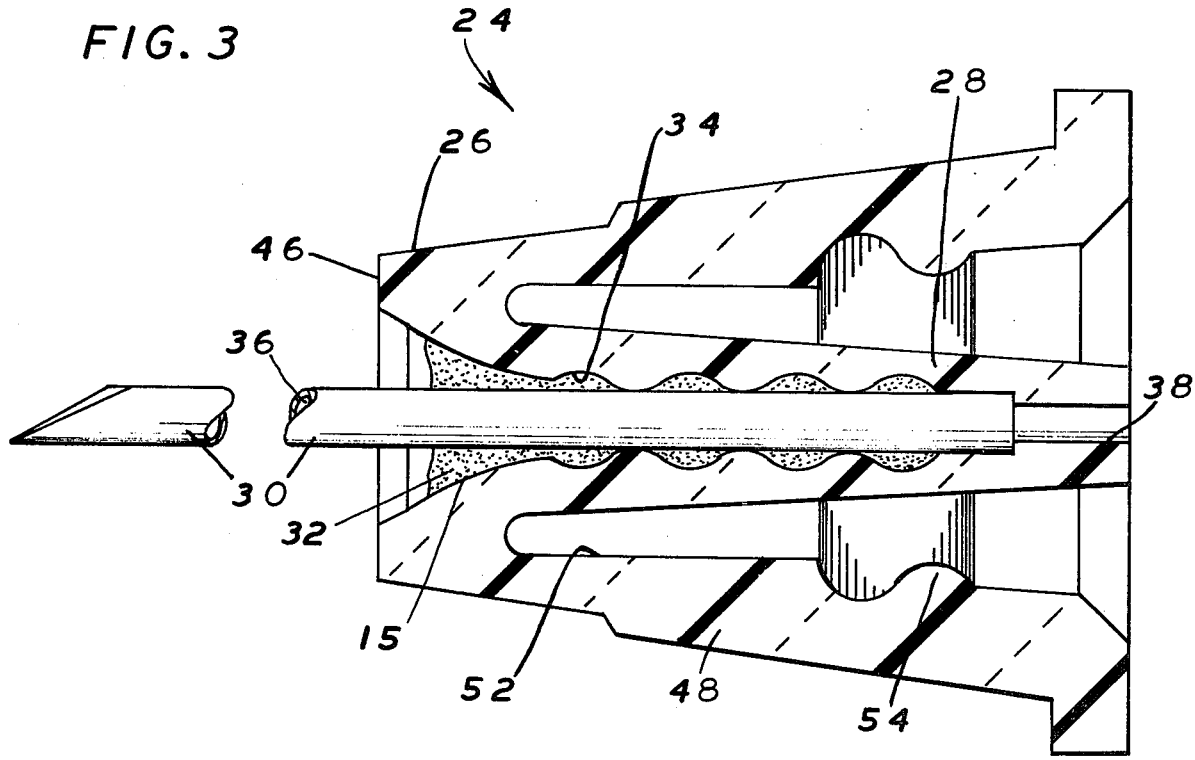
FIG. 3 is an enlarged sectional view of the needle assembly.

Referring to the drawings there is shown a low-dose hypodermic syringe including a barrel 10 into which is inserted a plunger assembly 12 for cooperating in expelling the contained liquid. Projecting from the distal end of the syringe barrel 10 is a reduced boss 14 having a female conical opening 16. The widened rear or proximal open end 18 cooperates in guiding the plunger assembly 12 into the barrel 10 at assembly of the syringe. The outward taper 22 serves as lead-in surfaces during assembly.

The needle assembly 24 comprises a needle hub 26 with a male conical extension 28 which matches the female conical opening 16 and cooperates in providing a liquid-tight seal therebetween. The cannula or needle 30 is secured in the needle hub 15 by means of a suitable epoxy cement 32 dispensed in annular recess 34 in such a way that the proximal end of its lumen or bore 36 is substantially coincident with the proximal end of the conical extension 28. However, as shown in the drawings, there may be a radially inwardly extending flange 38 at the end of the male conical extension 28 which serves as a stop when the needle is inserted into the said extension during assembly. The flange has a passageway or bore therein which generally conforms in size and dimension to the lumen 36 of the needle 30. Accordingly, it will be understood that the term "lumen" as used herein includes both the passageway in the needle 30 and passageway in any flange 38 of the male extension 28, which conforms in cross-sectional size to the bore of the needle 30.

When the needle assembly 24 is connected to the barrel 10 of the syringe and the male conical extension 28 is fully seated in the female conical opening 16, the proximal end of the needle hub is substantially flush with the roof 40 of the fluid chamber 42. Accordingly, there will be no significant residual volume beyond the volume of the chamber 42. Thus, the total volume within the syringe needle assembly will be substantially equal to the measured volume in the syringe. Above all, when extension 28 is inserted into the opening 16 of the boss 14 a substantially liquid tight seal will be formed to prevent leakage during the injection process.

Figure 6:
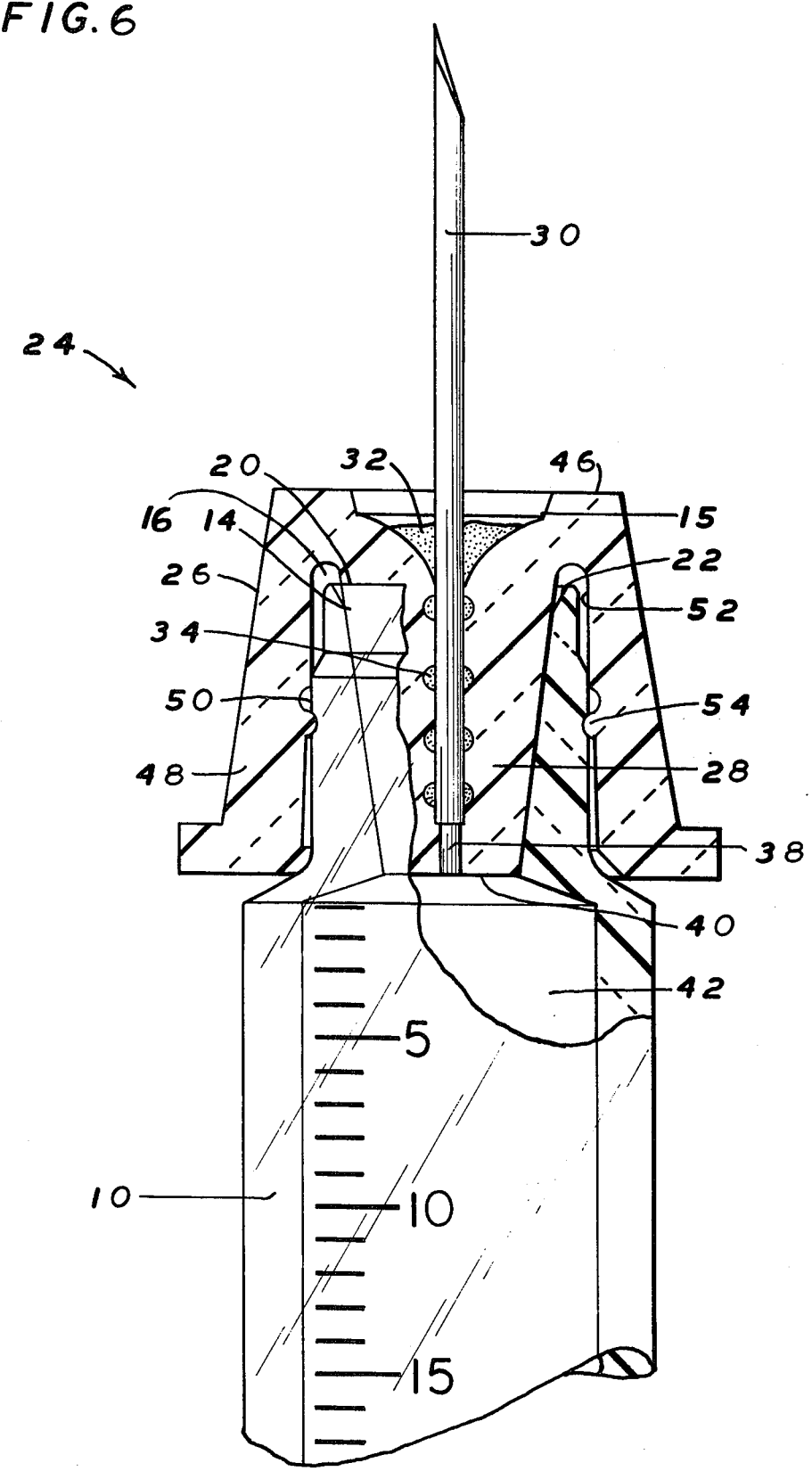
FIG. 6 is a fragmentary elevational view of the syringe barrel with attached needle assembly with certain parts broken away, removed and sectioned.

The distal end hub 15 has a flange 46 from which extends rearwardly a concentric collar 48. Collar 48 not only provides means for gripping the needle assembly for attaching and removing it from the barrel of the syringe, but functions to provide a mechanical lock of the needle assembly 24 to the syringe barrel 10. In this connection the interference fit between the mating surfaces 50 of the boss 14 and 52 of the collar 48 is supplemented by a radially inwardly extending flange or bead 54 which frictionally and tightly engages with boss surface 50. Inasmuch as the syringe barrel 10 and hub 24 are molded of a suitable resin, such as polypropylene, the bead 54 in time will form a depression in surface 50, as shown in FIG. 6 to complete the mechanical interlock. In this manner the seal between conical surfaces 16 and 28 is assured and maintained during removal of the needle sheath 56 and while the contained liquid is injected. Obviously, other forms of radially inwardly extending projections could be adapted in cooperating to form the mechanical lock between the needle assembly 24 and barrel 10.

Thus, among others, the several aforenoted objects and advantages are most effectively attained. Although a somewhat preferred embodiment of the invention has been disclosed and described in detail herein, it should be understood that the invention is in no sense limited thereby and its scope is to be determined by that of the appended claims.

What is claimed is:

1. A low-dose hypodermic syringe and attached needle assembly wherein:

the syringe includes a plastic tubular barrel having a distal end and a proximal end, a reduced boss having an exterior face extending from the distal end and defining an inner end wall, a piston in the barrel having a plunger rod extending from the proximal end of the barrel and the piston adapted to travel in the barrel into engagement with the barrel inner end wall in dispensing liquid from the syringe into the needle assembly;

the needle assembly includes a needle having a lumen and a pointed distal end and a proximal end and a plastic hub secured by cement to the needle at its proximal end, the hub including a radial flange and a tubular collar having one end integral with the flange and its other end extending towards the needle proximal end, the collar adapted to be manually gripped for attaching and removing the needle assembly from the barrel; and a connection joint attaching the needle assembly to the hypodermic syringe for cooperating in permitting fluid to be conveyed through the lumen from the fluid chamber to the pointed end of the needle comprising a female conical opening in the reduced boss, a conical male extension on the proximal end of the said hub and being inserted in the female opening, the shape and dimensions of the male extension matching the female opening whereby when the said extension is inserted into the said opening a leak proof seal will be provided by the matching surfaces of the female opening and male extension and the proximal end of such extension will be flush with the inner end wall of the barrel, the proximal end of the lumen substantially coincident with the proximal end of the extension so that there will be no residual volume of liquid beyond the measured volume of the barrel when the piston is extended fully into the barrel against the inner end wall; the collar having an annular radially inwardly extending bead for frictionally engaging with the outer surface of the reduced boss to provide a mechanical lock of the needle assembly on the syringe barrel, the collar having an inner face between the bead and flange providing an interference fit with the associated exterior surfaces of the reduced boss, the bead forming in time a corresponding depression in the boss outer surface thereby preventing the needle assembly from disassociation with the syringe barrel upon removal of a needle sheath and during the injection of the liquid in the barrel.

* * * * *

UNITED STATES PATENT OFFICE
CERTIFICATE OF CORRECTION

PATENT NO. : 4,040,421
DATED : August 9, 1977
INVENTOR(S) : H. Theodore Young

It is certified that error appears in the above-identified patent and that said Letters Patent are hereby corrected as shown below:

In the Abstract:

Line 1, before "The Connection" insert -- A hypodermic syringe includes a tubular barrel having a reduced boss at its distal end which defines an inner end wall.--

Signed and Sealed this

*First* Day *of November 1977*

[SEAL]

*Attest:*

RUTH C. MASON
*Attesting Officer*

LUTRELLE F. PARKER
*Acting Commissioner of Patents and Trademarks*